(12) United States Patent
Wiygul et al.

(10) Patent No.: US 12,144,937 B2
(45) Date of Patent: Nov. 19, 2024

(54) CATHETER SYSTEMS AND METHODS

(71) Applicant: Cornell University, Ithaca, NY (US)

(72) Inventors: Jeremy B. Wiygul, Flushing, NY (US); Simon Dunham, New York, NY (US); Bobak Mosadegh, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 472 days.

(21) Appl. No.: 17/630,785

(22) PCT Filed: Jul. 31, 2020

(86) PCT No.: PCT/US2020/044526
§ 371 (c)(1),
(2) Date: Jan. 27, 2022

(87) PCT Pub. No.: WO2021/026003
PCT Pub. Date: Feb. 11, 2021

(65) Prior Publication Data
US 2022/0288353 A1  Sep. 15, 2022

Related U.S. Application Data

(60) Provisional application No. 62/882,196, filed on Aug. 2, 2019.

(51) Int. Cl.
*A61M 25/00* (2006.01)
*A61M 25/10* (2013.01)

(52) U.S. Cl.
CPC .... *A61M 25/0074* (2013.01); *A61M 25/0017* (2013.01); *A61M 25/0097* (2013.01);
(Continued)

(58) Field of Classification Search
CPC .......... A61M 25/0074; A61M 25/0017; A61M 25/0097; A61M 25/1011;
(Continued)

(56) References Cited

U.S. PATENT DOCUMENTS 2,919,697 A    1/1960  Kyong
3,108,595 A *  10/1963 Overment ............. A61M 25/04
                                                     604/105
(Continued)

FOREIGN PATENT DOCUMENTS

GB    2395436 A *  5/2004  ........ A61M 25/0017

OTHER PUBLICATIONS

International Search Report and Written Opinion mailed Feb. 1, 2021 in PCT/US2020/044526.

*Primary Examiner* — Kai H Weng
*Assistant Examiner* — Alessandro R Del Priore
(74) *Attorney, Agent, or Firm* — McDermott Will & Emery LLP

(57) ABSTRACT

A catheter system is provided that reduces the risk of catheter-associated urinary tract infections by preventing bacteria near the urethral opening from being carried by the catheter during insertion, and by allowing cycling (filling and emptying) of the bladder. The system includes a main lumen, and a balloon near a distal end thereof that is inflatable, after insertion, to open an eyelet to the main lumen that allows urine to flow from the bladder into the main lumen. A catheter system with two balloons, e.g., a retention and an actuation balloon, is also provided herein. An access port at a proximal end has a resting configuration that closes the proximal end of main lumen to prevent drainage of urine through the main lumen. An access cap is provided that, when installed in the access port, opens the access port to allow urine to flow therethrough.

25 Claims, 10 Drawing Sheets

(52) U.S. Cl.
CPC . *A61M 25/1011* (2013.01); *A61M 2025/0037* (2013.01); *A61M 2025/0079* (2013.01)

(58) Field of Classification Search
CPC .. A61M 2025/0037; A61M 2025/0079; A61M 25/007; A61M 25/0075; A61M 25/10185; A61M 25/10; A61M 16/0475; A61M 25/04; A61B 1/00082
See application file for complete search history.

(56) References Cited

U.S. PATENT DOCUMENTS

| | | | | |
|---|---|---|---|---|
| 3,331,371 | A | | 7/1967 | Rocchi et al. |
| 4,813,935 | A | * | 3/1989 | Haber ............... A61M 25/0017 604/246 |
| 5,702,365 | A | * | 12/1997 | King ..................... A61M 29/02 604/105 |
| 6,203,526 | B1 | * | 3/2001 | McBeth ............. A61B 17/3415 604/246 |
| 2005/0101941 | A1 | | 5/2005 | Hakky et al. |
| 2005/0245900 | A1 | | 11/2005 | Ash |
| 2006/0253099 | A1 | * | 11/2006 | Noone .................. A61M 25/10 604/509 |
| 2009/0248059 | A1 | * | 10/2009 | Morsi ................ A61M 25/1011 606/200 |
| 2014/0336624 | A1 | * | 11/2014 | Adams, Jr. ........ A61M 25/1002 604/544 |

\* cited by examiner

CATHETER SYSTEMS AND METHODS

CROSS-REFERENCE OF RELATED APPLICATION

The present application is a United States National Phase under 35 U.S.C. § 371 of International Application No. PCT/US2020/044526 filed on Jul. 31, 2020, which claims the benefit of U.S. Provisional Patent Application No. 62/882,196, filed Aug. 2, 2019. The disclosure of each of the above-identified applications is incorporated herein by reference as if set forth in full.

FIELD OF THE INVENTION

The present subject matter relates generally to the field of medical devices, and more specifically to catheters for the collection or drainage of biological material.

BACKGROUND OF THE INVENTION

Indwelling catheters are commonly inserted into a patient's bladder through the urethra. These catheters can remain in the bladder for a period of time to continuously drain the bladder, particularly for patients who are unable to control the timing or completeness of urination due to injury, surgery, medication, or the like. However, particularly in cases in which the indwelling catheter remains in the bladder for significant periods of time, a catheter-associated (CA) urinary tract infection (UTI) can occur.

Catheter associated urinary tract infection (CA-UTI) is the single biggest cause of hospital acquired infection (HAI) both in the US and worldwide. The Centers for Disease Control (CDC) estimates that 40% of all HAI are CA-UTI, with over 500,000 reported in the US alone in 2009. Based on a per-UTI cost of $1000, the cost of CA-UTI per year in the US can be estimated to be $500 MM.

SUMMARY OF THE INVENTION

While catheter care standards to prevent CA-UTI have been shown to have some efficacy in reducing incidence of CA-UTI, and have been endorsed by the CDC, new catheter materials have had relatively little effect on incidence, and none of the conventional catheters that are widely used have successfully re-engineered the catheters themselves to attempt to reduce CA-UTI incidence.

The subject matter disclosed herein relates to a catheter system having various catheter system features that reduce the risk of urinary tract infection (UTI), relative to conventional catheters. These catheter system features include sealing features for closing the eyelet(s) at the distal end of the catheter to help prevent scooping of perimeatal bacteria, by the eyelet(s), during insertion of the catheter system into a subject's orifice. These sealing features thus help prevent the perimeatal bacteria from being carried by the catheter into the patient's bladder.

The catheter system features also include access features at the proximal end of the catheter that allow cycling (i.e., repeated filling and emptying) of the bladder, in contrast to the continuous draining of the bladder by a conventional catheter that leaves the bladder constantly decompressed. The access features allow the disclosed catheter systems to more closely replicate the natural operation of the bladder, forming a mechanical system that reduces the chances of any bacteria that is introduced into the bladder progressing into a full-blown infection. These and other features of the catheter systems and methods disclosed herein will be described in further detail hereinafter.

The catheter systems and methods disclosed herein may be used in all patients where an indwelling catheter for any length of time will be beneficial. This includes both pediatric and adult populations, and in inpatient, ICU, and outpatient settings.

The subject matter disclosed herein further relates to catheter system that includes a main tubular structure having an interior lumen, a proximal end, and a distal end. The system also includes a retention/actuation balloon located closer to the distal end than to the proximal end. The system also includes an eyelet located proximate to the actuation balloon that extends through the main tubular structure from an exterior surface through to the interior lumen. The eyelet is configured to be closed when the retention/actuation balloon is in a deflated configuration and to be opened by inflation of the retention/actuation balloon to an inflated configuration.

In some embodiments, the retention/actuation balloon is also the retention balloon of the system. In some embodiments, the system further includes a retention balloon that is distinct from the actuation balloon. In some embodiments, the retention balloon is located proximally to the actuation balloon along the main tubular structure.

In some embodiments, the system further includes an outer layer disposed on the exterior surface of the main tubular structure. In some embodiments, the outer layer includes a fenestration aligned with the eyelet, such that the outer layer is configured to be pulled by the inflation of the retention/actuation balloon, and the fenestration is configured to be pulled open by the pull on the outer layer to open the eyelet. In some embodiments, the retention/actuation balloon is formed, at least in part, by a cavity within the main tubular structure, such that the inflation of the retention/actuation balloon causes an expansion of the cavity, and the eyelet is configured to be pulled open by the expansion of the cavity. In some embodiments, the retention/actuation balloon is an interior retention/actuation balloon that is disposed within the interior lumen, such that the inflation of the retention/actuation balloon pushes open the eyelet from within the interior lumen. In some embodiments, the interior retention/actuation balloon includes an aperture through which a fluid in the interior lumen can flow.

In some embodiments, the system further includes a balloon port located proximate to the proximal end of the main tubular structure and a secondary lumen, where the secondary lumen extends along and parallel to the interior lumen between the balloon port and the proximal end of the retention/actuation balloon.

In some embodiments, the system further includes a balloon port located proximate to the proximal end of the main tubular structure and a secondary lumen, where the secondary lumen extends along and parallel to the interior lumen between the balloon port and the proximal edge of the retention balloon and between the distal edge of the retention balloon and the proximal edge of the actuation balloon, such that the actuation balloon and the retention balloon are inflated by injecting an inflation fluid or gas into both the actuation balloon and the retention balloon through the balloon port and the secondary lumen.

In some embodiments, the system further includes a first balloon port that is located proximate to the proximal end of the main tubular structure, and a secondary lumen, where the secondary lumen extends along and parallel to the interior lumen between the first balloon port and the retention balloon, such that the retention balloon is inflated by injecting an inflation fluid or gas into the retention balloon through the first balloon port and the secondary lumen; and a second balloon port that is located proximate to the proximal end of the main tubular structure, and a tertiary lumen, where the tertiary lumen extends along and parallel to the interior lumen between the second balloon port and the actuation balloon, such that the actuation balloon is inflated by injecting an inflation fluid or gas into the actuation balloon through the second balloon port and the tertiary lumen.

In some embodiments, the system is configured such that inflation of the retention balloon is independent of inflation of the actuating balloon.

In some embodiments, the system further includes an access port located proximate to the proximal end of the main tubular structure. In some embodiments, the access port includes a dilating diaphragm having a resting configuration in which an access point in the dilating diaphragm is closed to prevent fluid from flowing from the interior lumen through the access port. In some embodiments, the system further includes an access cap configured to couple to the access port, and to open the access point in the dilating diaphragm when coupled to the access port.

In some embodiments, the access cap includes a base, a beak extending from the base, and at least one beak eyelet extending through the beak to a cavity formed within the beak. In some embodiments, the beak is configured to press open the access point of the dilating diaphragm, and to extend through the dilating diaphragm so that, when the access cap is coupled to the access port, at least one beak eyelet fluidly couples the interior lumen of the main tubular structure to the cavity within the beak. In some embodiments, the cavity within the beak extends through the base of the access cap to an opening that is located proximate to the proximal end of the access cap, such that the opening is configured to be coupled to one of a plurality of drainage destinations.

The subject matter disclosed herein further relates to a method. The method includes inserting, into a bladder of a patient, a distal end of a main tubular structure having an interior lumen, a proximal end, and a distal end. The method also includes inflating a retention/actuation balloon that is located proximate to the distal end of the main tubular structure. The method also includes opening, by inflating the retention/actuation balloon, a closed eyelet located proximate to the retention/actuation balloon, where the eyelet extends through the main tubular structure from an exterior surface to the interior lumen.

In some embodiments, the actuation balloon of the system is also a retention balloon. In some embodiments, the method also includes inflating a retention balloon that is distinct from the actuation balloon, where the retention balloon is located proximally with respect to the actuation balloon along the main tubular structure. In some embodiments, the retention balloon and the actuation balloon are inflated by injecting an inflation fluid or gas into the balloons through a single balloon port. In some embodiments, the retention balloon and the actuation balloon are inflated by injecting an inflation fluid or gas into the balloons through two separate balloon ports, such that inflation of the retention balloon is independent of the inflation of the actuating balloon.

In some embodiments, the method also includes preventing fluid from flowing from the interior lumen through an access port proximate to the proximal end of the main tubular structure, with a dilating diaphragm proximate to the proximal end of the main tubular structure. In some embodiments, the method also includes coupling an access cap to the access port to allow the fluid to flow from the interior lumen through the access port and the access cap. In some embodiments, coupling the access cap to the access port includes passing a beak of the access cap through the dilating diaphragm until a beak eyelet on the beak fluidly couples the interior lumen to a cavity within the access cap. In some embodiments, coupling the access cap to the access port includes engaging a pair of flanges on the access cap with corresponding mounting features on the access port. In some embodiments, the method also includes removing the access cap, to prevent flow of the fluid from the interior lumen through the access port. In some embodiments, removing the access cap includes pinching a pair of tabs to disengage the pair of flanges from the corresponding mounting features.

The subject matter disclosed herein further relates to catheter system that includes a main tubular structure having an interior lumen, a proximal end, and a distal end. The system also includes an eyelet, located closer to the distal end, openable via inflation of a balloon located closer to the distal end. The system also includes an access port, located proximate to the proximal end, and configured to be selectively opened and closed to control egress of a fluid from the interior lumen.

The subject matter disclosed herein further relates to a method. The method includes inserting, into a fluid reservoir, a distal end of a main tubular structure having an interior lumen, a proximal end, and a distal end. The method also includes inflating a retention/actuation balloon located proximate the distal end of the main tubular structure. The method also includes opening, by inflating the retention/actuation balloon, a closed eyelet located proximate to the actuation balloon, where the eyelet extends through the main tubular structure from an exterior surface to the interior lumen. The method also includes collecting fluid from the fluid reservoir through the eyelet and the interior lumen.

DETAILED DESCRIPTION OF THE INVENTION

Currently available catheters are predisposed to collect perimeatal bacteria as they are advanced into the urinary tract, which can inadvertently cause a UTI. These conventional catheters are also designed to maintain the bladder in a drained, collapsed state. Therefore, there is currently a need in the medical field for a catheter system, minimizes transportation of perimeatal bacteria into the urinary tract and bladder, and/or which allows cycling of the bladder.

Figure 1:
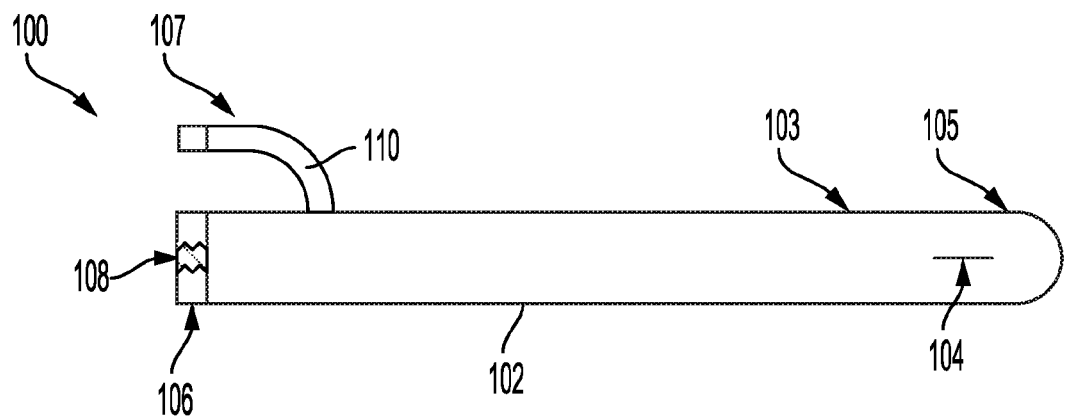
FIG. 1 represents a long-axis side view of a catheter system before introduction into a patient's bladder, according to aspects of the disclosure.

The subject matter disclosed herein relates to a catheter system 100 including a main tubular structure 102, having a proximal end 107 and a distal end 105, as shown in FIG. 1. As shown in FIG. 1, the distal end 105 of main tubular structure 102 is closed, such that a closed end lumen is formed within main tubular structure 102. An egress point for the catheter system is formed at an access port 106 provided at the proximal end of main tubular structure 102. Access port 106 is accessible with an access cap. For example, a one way valve may be provided at the egress point that can be accessed by inserting an access cap that, when passed through the one way valve of the egress point, allows the flow of urine from the patient's bladder and through the catheter, as will be described in further detail hereinafter.

Mounting features 108 such as a roughened exterior surface or click-mate feature, can be provided on the exterior surface of access port 106 and/or structure 102 to facilitate attachment of the access cap.

As shown in FIG. 1, catheter system 100 includes a fenestration 104 at the distal end of main tubular structure 102. In the configuration shown in FIG. 1, fenestration 104 is in a closed configuration. However, a retention/actuation balloon 103, deflated in the configuration of FIG. 1, is also provided at the distal end of main tubular structure 102. When retention/actuation balloon 103 is inflated (e.g., by providing a fluid or a gas, such as water, air, saline, or another suitable biocompatible fluid or gas into retention/actuation balloon 103 via balloon port 110 at the proximal end 107), fenestration 104 can be opened to allow fluid communication between the internal lumen of tubular structure 102 and the environment exterior to main tubular structure 102.

Figure 2:
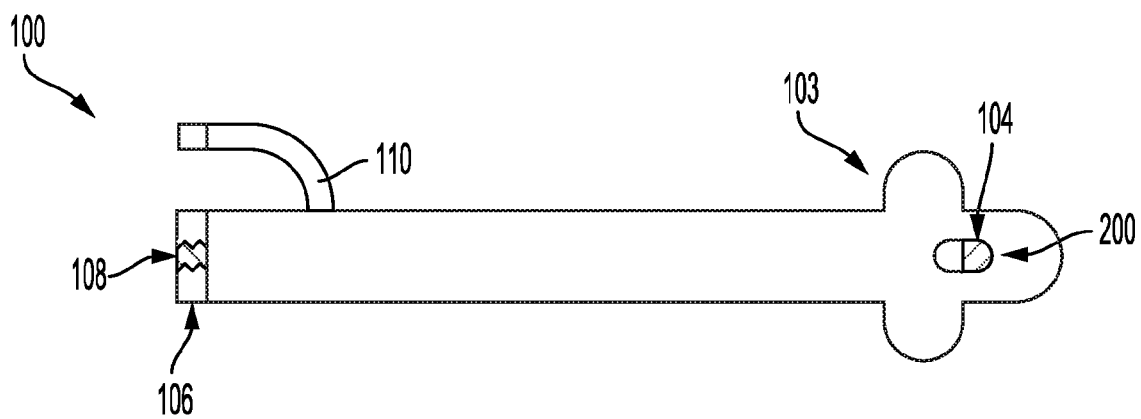
FIG. 2 represents a long-axis side view of the catheter system of FIG. 1 after introduction into the patient's bladder and inflation of a retention/actuation balloon, according to aspects of the disclosure.

For example, following insertion of the distal end 105 of main tubular structure 102 into the bladder of a patient (e.g., via the urethra), retention/actuation balloon 103 can be inflated as shown in FIG. 2. FIG. 2 also shows how, when retention/actuation balloon 103 is inflated, fenestration 104 is pulled and/or stretched into an open configuration. In the configuration of FIG. 2, an eyelet 200 in main tubular structure 102 is exposed to the exterior environment (e.g., the interior of the patient's bladder) by the open fenestration 104. In this way, fluid such as urine within the patient's bladder can be allowed to pass through fenestration 104 and eyelet 200 into the interior lumen of main tubular structure 102. In some implementations, insertion of the distal end 105 of main tubular structure 102 into other fluid reservoirs, e.g., fluid reservoirs outside of a human or animal body, such as fluid reservoirs in chemical reactors, HVAC systems, or other pieces of industrial or scientific equipment, may allow collecting or sampling of fluids from the other fluid reservoirs through the eyelet and the interior lumen.

Because fenestration 104 is closed, and covers eyelet 200, during insertion of main tubular structure 102 through the patient's urethra into the patient's bladder, the eyelet is prevented from scooping bacteria, such perimeatal bacteria, into the urinary tract and bladder from the outer edge of the urethra. In this way, the risk of CA-UTI can be reduced.

Figure 3:
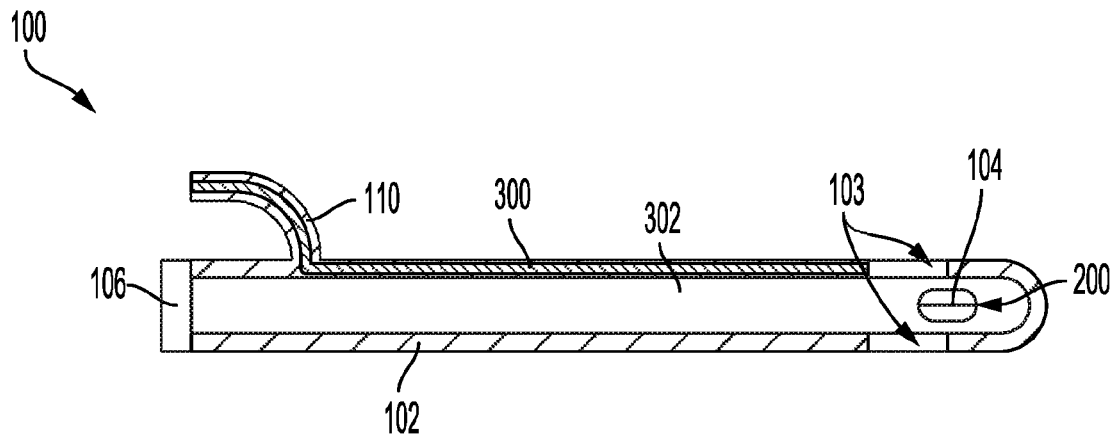
FIG. 3 represents a long-axis cross-sectional view of the catheter system of FIG. 1 before introduction into the patient's bladder, according to aspects of the disclosure.
Figure 4:
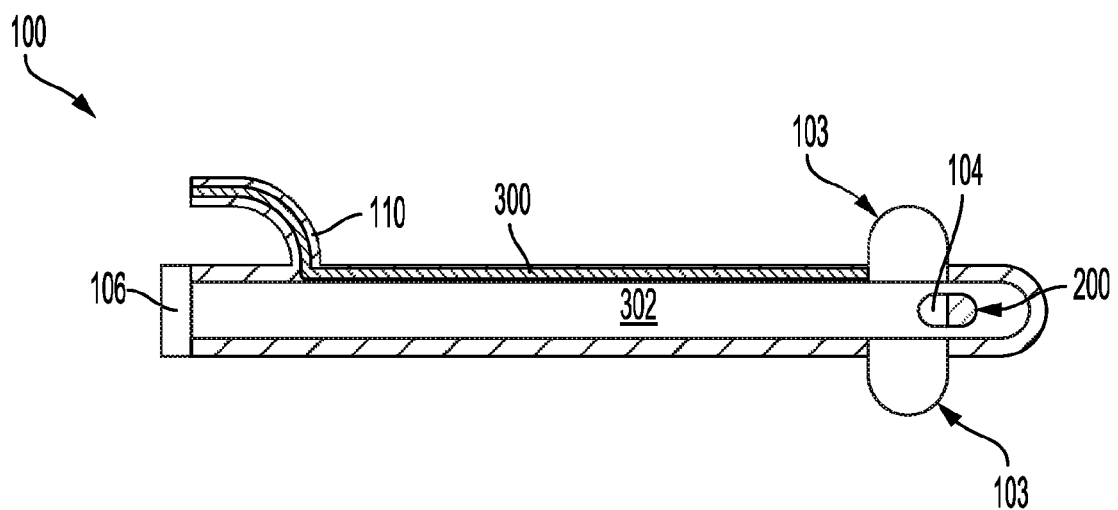
FIG. 4 represents a long-axis cross-sectional view of the catheter system of FIG. 1 after introduction into the patient's bladder and inflation of the retention/actuation balloon, according to aspects of the disclosure.

FIGS. 3 and 4 show cross-sectional views of catheter system 100 in the configurations of FIGS. 1 and 2, respectively. In the cross-sectional views of FIGS. 3 and 4, the internal lumen 302 of main tubular structure 102 can be seen. An open eyelet 200, covered by closed fenestration 104 is shown in FIG. 3. The open eyelet 200, in line with the opened fenestration 104, which has been pulled and/or stretched open by the inflation of retention/actuation balloon 103, is shown in FIG. 4. In the cross-sectional views of FIGS. 3 and 4, a secondary lumen 300 can be seen extending between balloon port 110 and balloon 103, through which inflation fluid or gas can be passed. In these examples, secondary lumen 300 is formed as a cavity within a monolithic main tubular structure 102. However, this is merely illustrative, and main tubular structure 102 can alternatively be formed by multiple layers arranged to form interior lumen 302, secondary lumen 300, balloon 103, and eyelet 200.

In the examples of FIGS. 1-4, fenestration 104 is formed in an outer layer of catheter system 100, the outer layer being formed on the outer surface of main tubular structure 102. Further details of the arrangement of this outer layer will be described hereinafter in connection with FIGS. 8 and 9.

Figure 5:
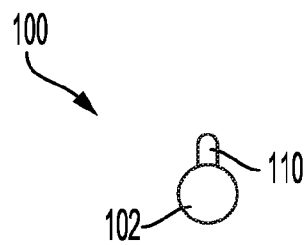
FIG. 5 represents a front view of the catheter system of FIG. 1 with the retention/actuation balloon deflated, according to aspects of the disclosure.
Figure 6:
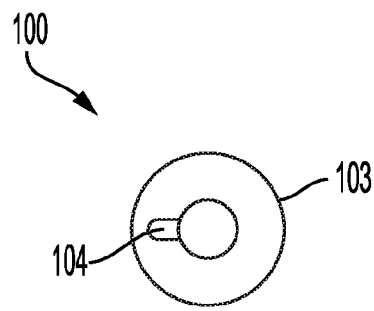
FIG. 6 represents a front view of the catheter system of FIG. 1 with the retention/actuation balloon deflated, according to aspects of the disclosure.

First, however, FIGS. 5 and 6 show front views of catheter system 100 in deflated and inflated configurations for balloon 103, respectively. In the deflated configuration of FIG. 5, the balloon port 110 can be seen from the front end of catheter system 100. In the inflated configuration of FIG. 6, the inflated balloon 103, and the open fenestration 104 can be seen from the front end of catheter system 100.

Figure 7:
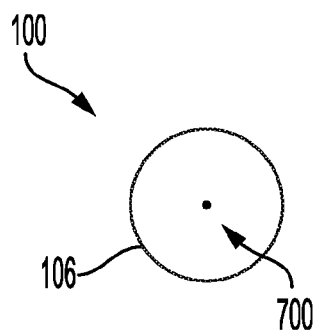
FIG. 7 represents a rear view of the catheter system of FIG. 1 with the retention/actuation balloon inflated, according to aspects of the disclosure.

FIG. 7 shows a rear view of catheter system 100, in which an access point 700 in access port 106 can be seen. Access point 700 may be, for example, a dilating diaphragm having a potential space at the center that can be expanded by insertion of a beak of an access cap, to provide fluid access to interior lumen 302, as discussed in further detail hereinafter. In the example of FIG. 7, the dilating diaphragm is in a resting configuration in which access point 700 is closed to prevent fluid from flowing from the interior lumen through the access port.

As discussed above in connection with FIGS. 1-4, fenestration 104 may be formed in an outer layer of catheter system 100, the outer layer being formed on the outer surface of main tubular structure 102.

Figure 8:
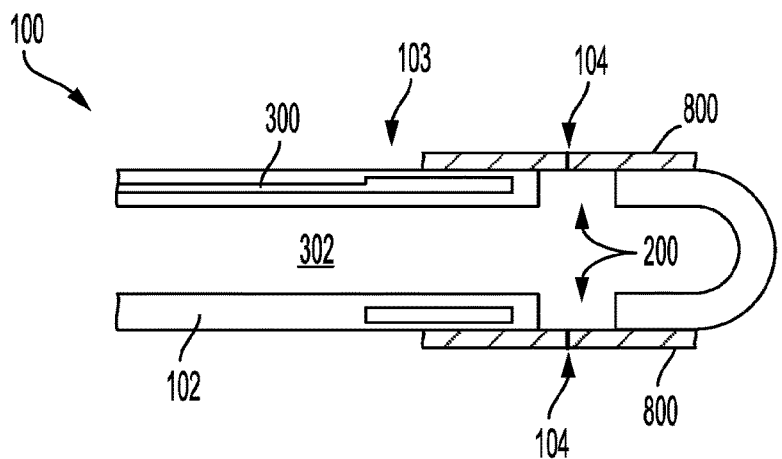
FIG. 8 represents a long-axis cross-sectional view of the catheter system of FIG. 1, rotated by ninety degrees with respect to the view represented in FIG. 3, and before introduction into the patient's bladder, according to aspects of the disclosure.

FIG. 8 illustrates an example in which an outer layer 800, having a fenestration 104 located over (e.g., aligned with) each eyelet 200 in main tubular structure 102, is provided on the outer surface of main tubular structure 102. In the example of FIG. 8, balloon 103 is deflated and fenestrations 104 are closed, covering the eyelets 200. In this configuration, opposing sidewalls of layer 800, each extending through the thickness of layer 800 on a corresponding side of fenestration 104, are substantially in contact, thus closing the fenestration and the underlying eyelet.

Figure 9:
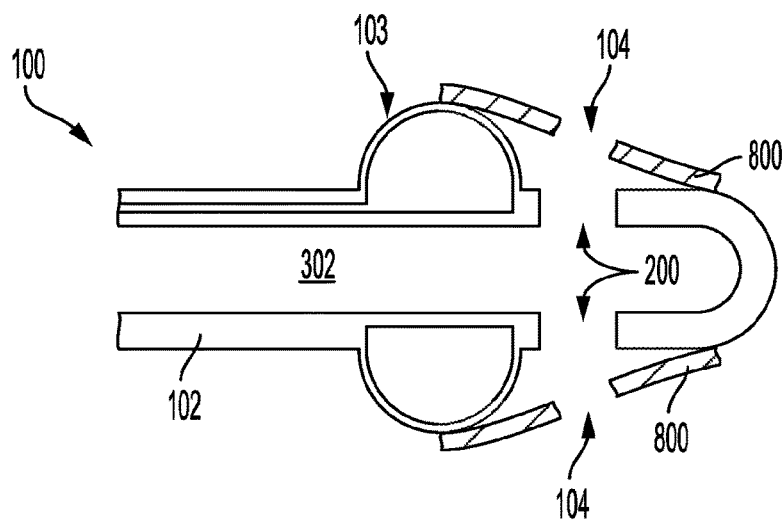
FIG. 9 represents a long-axis cross-sectional view of the catheter system of FIG. 1, rotated by ninety degrees with respect to the view represented in FIG. 4, and after introduction into the patient's bladder and inflation of the retention/actuation balloon, according to aspects of the disclosure.

FIG. 9 illustrates a configuration in which balloon 103 has been inflated by fluid or gas flowing through secondary lumen 300. The inflation of balloon 103 has caused the outer layer 800 to be pulled apart, responsive to the expansion of the cavity in main tubular structure 102 that forms balloon 103, to open fenestrations 104. In this way, a gap is formed between the opposing sidewalls of each fenestration, as shown, to allow fluid to flow through the fenestration.

In the examples of FIGS. 8 and 9, outer layer 800 is shown extending from a location on top of balloon 103 to a location, beyond eyelets 200, near the distal tip of main tubular structure 102. However, in various configurations, outer layer 800 can extend continuously around the distal tip, and/or extend over the entirety of balloon 103 and/or the entire length of main tubular structure. In order to ensure that the overall thickness of catheter system 100 is not increased in a way that increases discomfort or difficulty of insertion, outer layer 800 may have a thickness of less than, for example, 2 millimeters above the outer surface of main tubular structure 102.

In the example of FIG. 9, when balloon 103 is inflated, portions of outer layer 800 are allowed to separate from the outer surface of main tubular structure 102, such that a cavity is formed between the open fenestration 104 and the eyelet 200. Fluid that may accumulate in this cavity may be squeezed, from the cavity, either back into the bladder via fenestration 104 or into interior lumen 302 when balloon 103 is deflated.

Main tubular structure 102 may be formed from any flexible or semi-flexible material including latex, silicone, or Teflon or any polymer that is biocompatible with a subject's body and will not cause undue discomfort. Outer layer 800 may be formed from the same material as main tubular structure 102 or a different material (e.g., a different one, or a different combination, of latex, silicone, or Teflon or any polymer that is biocompatible with a subject's body and will not cause undue discomfort).

Balloon 103 may be formed from a thinned portion of main tubular structure 102 associated with a cavity within structure 102, or may be formed from a layer of a multi-layer main tubular structure, in various examples.

Figure 10:
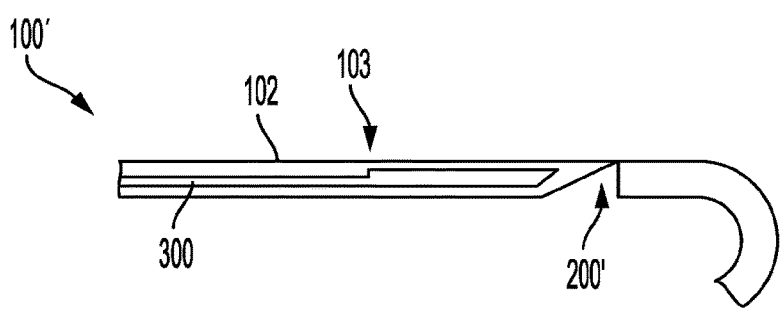
FIG. 10 represents a long-axis cross-sectional view of a portion of another catheter system, rotated by ninety degrees with respect to the view represented in FIG. 3, and before introduction into the patient's bladder and with a retention/actuation balloon deflated, according to aspects of the disclosure.
Figure 11:
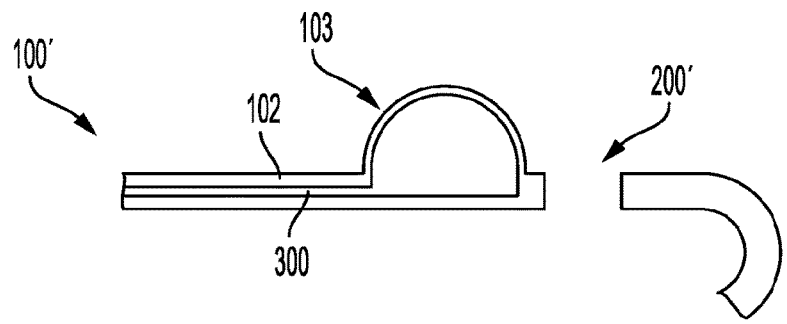
FIG. 11 represents a long-axis cross-sectional view of the catheter system of FIG. 10, after inflation of the retention/actuation balloon, according to aspects of the disclosure.

Although the examples of FIGS. 1-4, 8, and 9 include an outer layer 800 with fenestrations 104 that are closable to cover and close eyelets 200 in main tubular structure 102, it should be appreciated that other configurations of a catheter system with eyelets that are closed during insertion (e.g., and prior to inflation of a retention/actuation balloon) are contemplated. For example, FIGS. 10 and 11 respectively show deflated and inflated configurations of an alternative catheter system 100' having a distal end in which an eyelet 200' itself is closed in the deflated configuration (e.g., prior to and/or during insertion) of main tubular structure 102. As shown in FIG. 11, in this configuration, when balloon 103 is inflated, a portion of main tubular structure 102 is pulled by the inflating balloon (e.g., away from an opposing portion of main tubular structure 102) to open the eyelet 200'.

Turing now to FIGS. 12-21, a description of the access features at the proximal end 107 of catheter system 100 will be provided. It should also be noted that the access features of FIGS. 12-21 can also be used at the proximal end of catheter system 100' of FIGS. 10 and 11, and/or the catheter system 2200 to be described hereinafter in connection with FIGS. 22-26.

Figure 12:
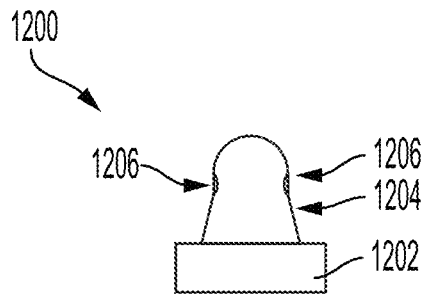
FIG. 12 represents a side view of an access cap for a catheter system, according to aspects of the disclosure.

FIG. 12 shows a side view of an access cap 1200 that can be mated with access port 106 described herein (see, e.g., FIG. 1), to allow fluid to flow out of interior lumen 302 (e.g., to withdraw a specimen of urine, to allow continuous drainage from the bladder into a urine collection bag, to allow the urine to be discharged into a toilet or other receptacle, and/or to allow irrigation of the catheter via a syringe). Because, as described in further detail hereinafter, urine cannot flow out of interior lumen 302 unless access cap 1200 is engaged with access port 106, the patient's bladder can be allowed to fill and empty cyclically, mimicking the natural function of the bladder, and further preventing bacteria that may be introduced into the bladder from causing a full-blown infection.

In the side view of FIG. 12, it can be seen that access cap 1200 can be provided with a flexible base 1202 (e.g., a rubber base), and relatively more rigid beak 1204 (e.g., a beak formed from a rigid polymer such as a plastic). Base 1202 can include features for attaching various drainage vessels or tubing to catheter system 100. Beak 1204 is configured to pierce access point 700 of access port 106, when access cap 1200 is inserted into access port 106. As shown, beak 1204 includes two beak eyelets 1206. Beak eyelets 1206 form drainage holes for catheter system 100 when access cap 1200 is engaged with access port 106.

Figure 13:
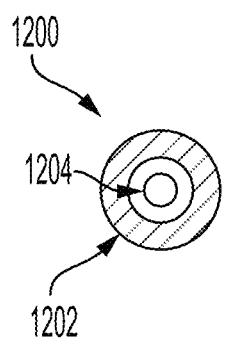
FIG. 13 represents a top view of the access cap of FIG. 13, according to aspects of the disclosure.
Figure 14:
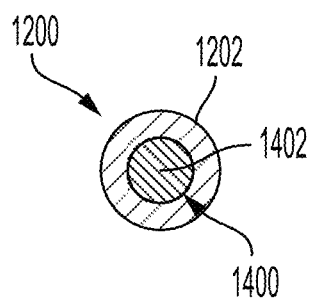
FIG. 14 represents a bottom view of the access cap of FIG. 13, according to aspects of the disclosure.
Figure 15:
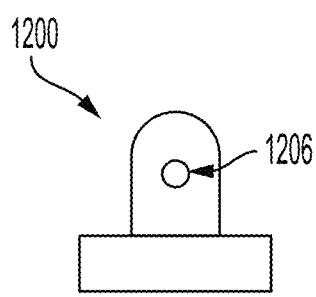
FIG. 15 represents a side view of the access cap of FIG. 13, rotated ninety degrees from the view represented in FIG. 12, according to aspects of the disclosure.

FIG. 13 shows a top view of access cap 1200, and FIG. 14 shows a bottom view of access cap 1200, in which an opening 1400 in flexible base 1202 can be seen leading to a cavity 1402 within the access cap. FIG. 15 shows another side view of access cap 1200, rotated ninety degrees relative to the side view of FIG. 12, to provide a face-on view of one of beak eyelets 1206.

Figure 16:
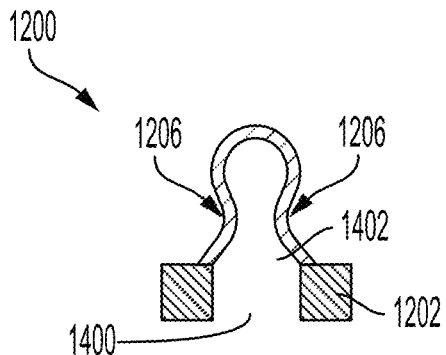
FIG. 16 represents a cross-sectional side view of the access cap of FIG. 13, according to aspects of the disclosure.
Figure 17:
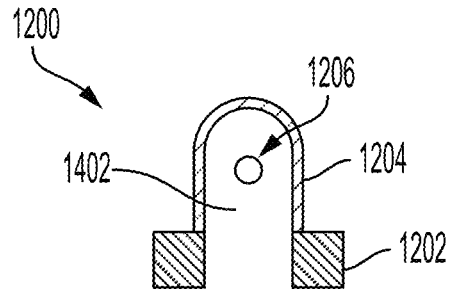
FIG. 17 represents a cross-sectional side view of the access cap of FIG. 13, rotated ninety degrees from the view represented in FIG. 16, according to aspects of the disclosure.

FIG. 16 shows a cross-sectional side view of access cap 1200, in the same orientation as the side view of FIG. 12. In the example of FIG. 16, cavity 1402 can be seen. As shown, cavity 1402 forms space within both beak 1204 and base 1202, and is fluidly coupled to the environment external to access cap 1200 by beak eyelets 1206 and the hole 1400 in base 1202. Fluid that flows through beak eyelets 1206 into cavity 1402 can exit cavity 1402 via the opening 1400. FIG. 17 shows another cross-sectional side view of access cap 1200, rotated ninety degrees relative to the side view of FIG. 16, to provide a face-on view of one of beak eyelets 1206.

In some configurations, beak 1204 and base 1202 may be arranged to engage with access port 106 at the proximal end of main tubular structure 102 without other attachment features (e.g., via a press fit, or a snap fit with the internal surface of main tubular structure 102). In other configurations, access cap 1200 may be provided with additional attachment features, such as flanges 1800, as shown in FIG. 18.

Figure 18:
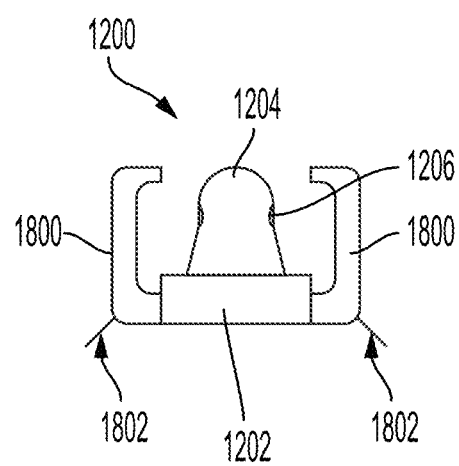
FIG. 18 represents a side view of an access cap having attachment flanges, according to aspects of the disclosure.

As shown in the example of FIG. 18, two flanges 1800 may extend outward from opposing sides of base 1202, and then curve to extend along the length of access cap 1200, separated from beak 1204. In this way, flanges 1800 are arranged to grasp the outer surface of main tubular structure 102 (e.g., by engaging with features 108 of FIG. 1) to secure access cap 1200 to main tubular structure 102. A pair of tabs 1802 extending rearward from flanges 1800 can be pinched to rotate the flanges outward for installation and/or removal of access cap 1200.

Figure 19:
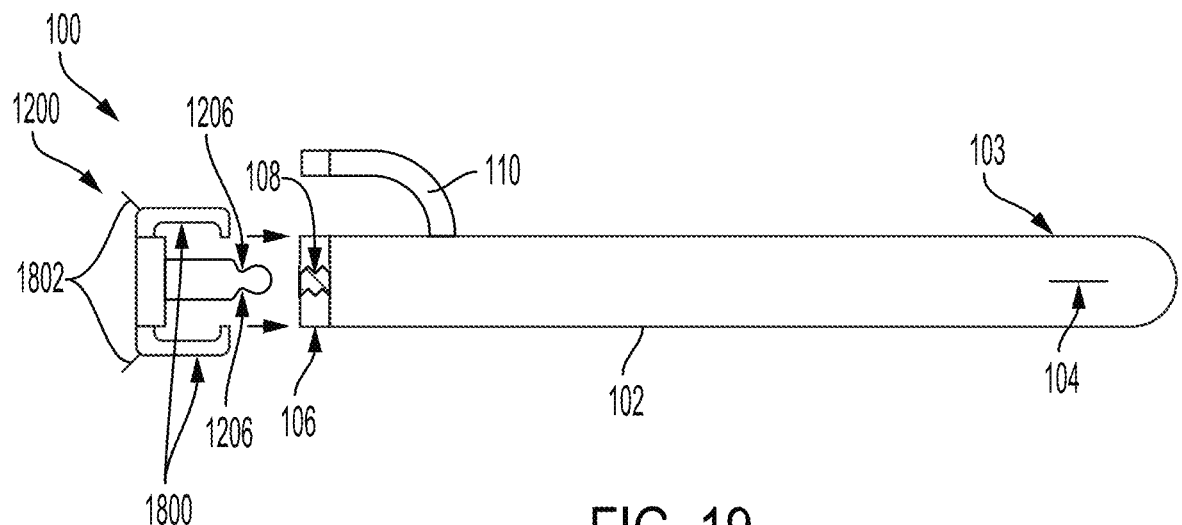
FIG. 19 represents a long-axis view of the catheter system of FIG. 1 with the access cap of FIG. 18 removed from an access port of the catheter, according to aspects of the disclosure.

FIG. 19 shows a long-axis view of catheter system 100 in which access cap 1200 is positioned for coupling to access port 106. As indicated by the arrows in the figure, access cap 1200 can be coupled to main tubular structure 102 by inserting the beak of the access cap into access port 106.

Figure 20:
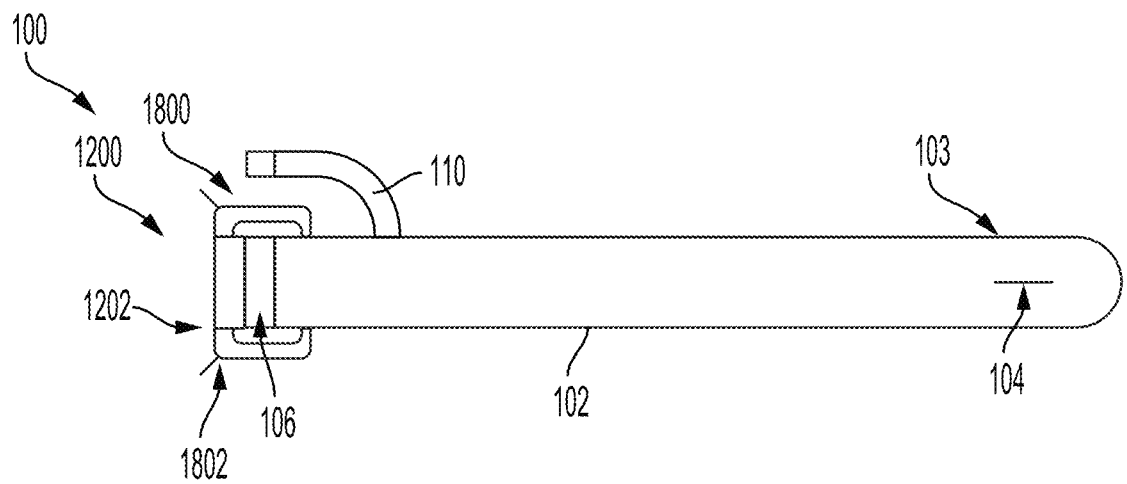
FIG. 20 represents a long-axis view of the catheter system of FIG. 1 with the access cap of FIG. 18 inserted into the access port of the catheter, according to aspects of the disclosure.
Figure 21:
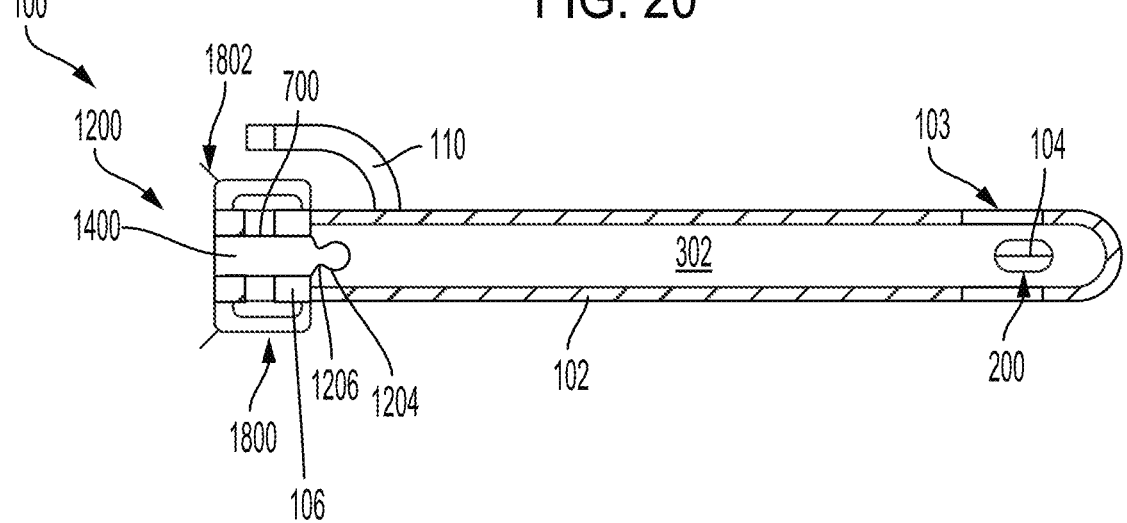
FIG. 21 represents a long-axis cross-sectional view of the catheter system of FIG. 20, according to aspects of the disclosure.

FIG. 20 shows a long-axis view of catheter system 100 in which beak 1204 has been inserted into access port 106, and access cap 1200 is coupled to access port 106 and held in place by flanges 1800. FIG. 21 shows a cross-sectional view of catheter system 100 in the configuration of FIG. 20. In the cross-sectional view of FIG. 21, it can be seen that beak 1204 has pierced access port 106. By opening the potential space of the dilating diaphragm of access point 700, such that beak eyelets 1206 fluidly couple interior lumen 302 to an egress point corresponding to opening 1400 of access cap 1200, the installed access cap 1200 allows fluid to drain from interior lumen 302 through the access cap. By removing the access cap, drainage can be stopped, to allow the patient's bladder to fill for later emptying by re-attachment of access cap 1200, or attachment of another access cap 1200, to access port 106.

In the examples of FIGS. 1-11 and 19-21, an example catheter system is described in which a balloon 103 that is disposed at (e.g., integrally formed with) the outer surface of main tubular structure 102 expands to open eyelets 200 (e.g., directly or by opening fenestrations 104 in a layer above the eyelets). However, in another example, a catheter system 2200 may be provided in which a balloon that is disposed interior to the main tubular structure opens the eyelets at the distal end of a main tubular structure.

Figure 22:
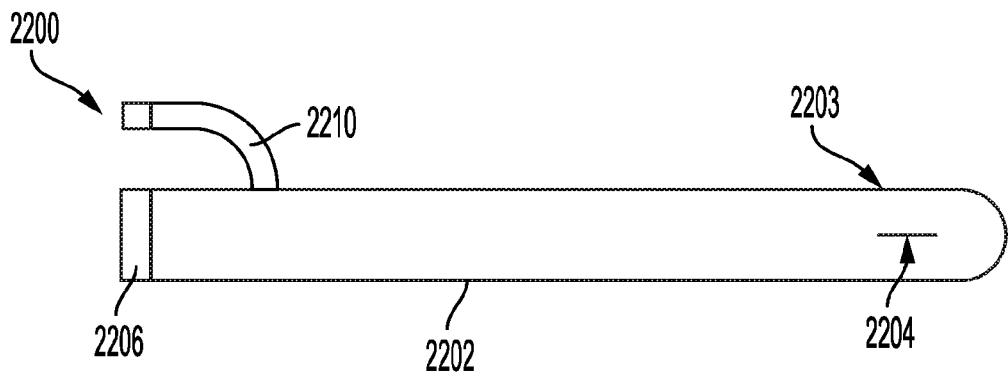
FIG. 22 represents a long-axis side view of another catheter system before introduction into a patient's bladder, according to aspects of the disclosure.

For example, FIG. 22 illustrates a catheter system 100 including a main tubular structure 2202, having a proximal end and a distal end, in which the distal end of main tubular structure 2202 is closed, such that a closed end lumen is formed within main tubular structure 2202. An access port 2206 (e.g., configured with an access point 700 and arranged to receive access cap 1200 as described herein in connection with access port 106) is provided at the proximal end of main tubular structure 2202. Although not shown in FIG. 22, mounting features such as a roughened exterior surface or click-mate feature, can be provided on the exterior surface of access port 2206 to facilitate attachment of the access cap.

As shown in FIG. 22, catheter system 2200 includes an eyelet 2204 at the distal end of main tubular structure 2202. In the configuration shown in FIG. 22, eyelet 2204 is in a closed configuration. However, a retention/actuation balloon, interior to main tubular structure 2202 and deflated and not visible in the configuration of FIG. 2, is also provided at the distal end of main tubular structure 2202. When the interior retention/actuation balloon is inflated (e.g., by providing a fluid or a gas, such as water, air, saline, or another suitable biocompatible fluid or gas into the interior retention/actuation balloon via balloon port 2210 at the proximal end), expandable portion 2203 of main tubular structure 2202 expands, and eyelet 2204 can be opened to allow fluid communication between the internal lumen of tubular structure 2202 and the environment exterior to main tubular structure 2202.

Figure 23:
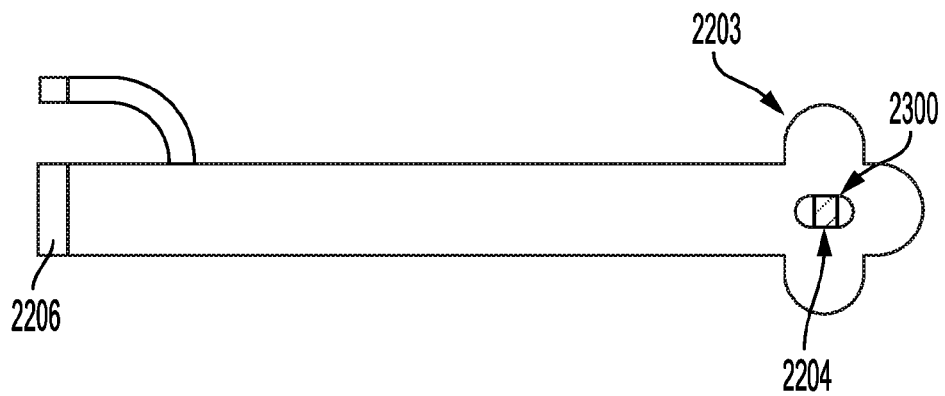
FIG. 23 represents a long-axis side view of the catheter system of FIG. 22 after introduction into the patient's bladder and inflation of an interior retention/actuation balloon, according to aspects of the disclosure.

For example, following insertion of the distal end of main tubular structure 2202 into the bladder of a patient (e.g., via the urethra), an interior retention/actuation balloon 2300 can be inflated as shown in FIG. 23. FIG. 23 also shows how, when interior retention/actuation balloon 2300 is inflated, eyelet 2204 is pushed from within into an open configuration. In the configuration of FIG. 23, a portion of interior balloon 2300 can be seen through the open eyelet 2204, and the open eyelet 2204 fluidly couples a main interior lumen in main tubular structure 2202 to the exterior environment (e.g., the interior of the patient's bladder). In this way, fluid such as urine within the patient's bladder can be allowed to pass through open eyelet 2204 and into the interior lumen of main tubular structure 2202. In some implementations, insertion of the distal end of main tubular structure 2202 into other fluid reservoirs, e.g., fluid reservoirs outside of a human or animal body, such as fluid reservoirs in chemical reactors, HVAC systems, or other pieces of industrial or scientific equipment, may allow collecting or sampling of fluids from the other fluid reservoirs through the eyelet and the interior lumen.

Because eyelet 2204 is closed during insertion of main tubular structure 2202 through the patient's urethra into the patient's bladder, the eyelet is prevented from scooping bacteria, such perimeatal bacteria, into the urinary tract and bladder from the outer edge of the urethra. In this way, the risk of CA-UTI can be reduced.

As can be seen in the example of FIG. 23, the length of balloon 2300, along the long axis of main tubular structure 2202 is less than the length of the open eyelet 2204, so that fluid can flow around balloon 2300, through the open eyelet 2204, into the interior lumen of main tubular structure 2202. A front view of balloon 2300 is shown in FIG. 24.

Figure 24:
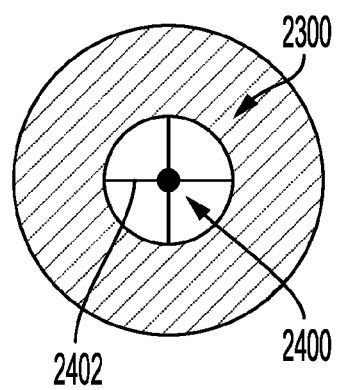
FIG. 24 represents a front view of the interior retention/actuation balloon of FIG. 23, according to aspects of the disclosure.

In the example of FIG. 24, balloon 2300 is seen to be a ring-shaped balloon having an aperture 2400 through which fluid can flow. A support structure 2402 may be provided to hold the aperture open, even when balloon 2300 is inflated (e.g., for retention of main tubular structure 2202 in the patient's bladder and for actuating opening of eyelet(s) 2204).

Figure 25:
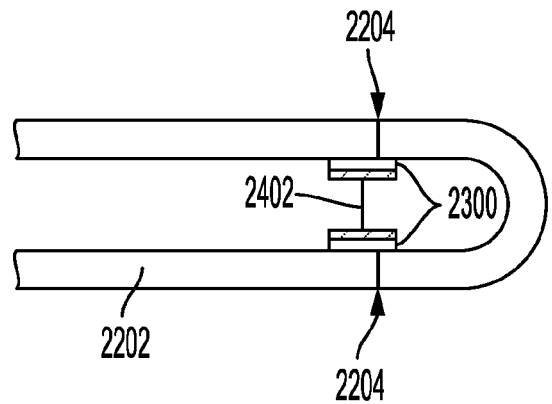
FIG. 25 represents a cross-sectional view of a portion of the catheter system of FIG. 22, according to aspects of the disclosure.
Figure 26:
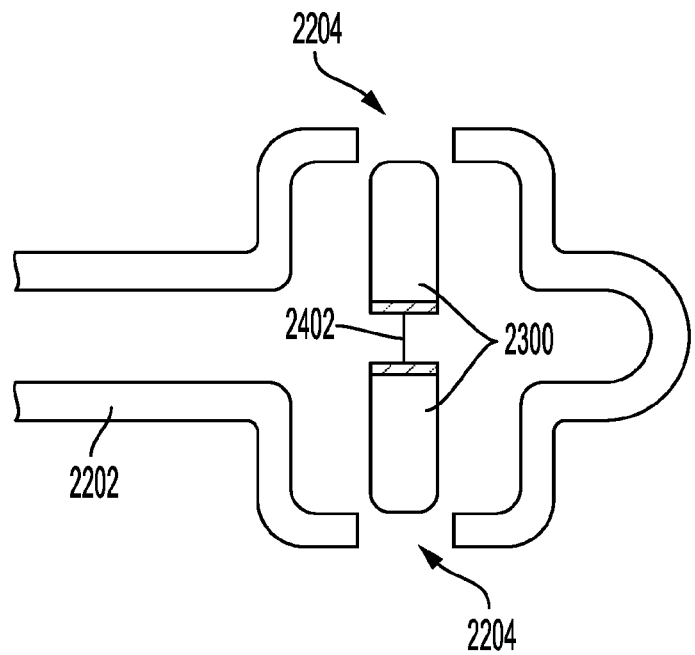
FIG. 26 represents a cross-sectional view of a portion of the catheter system of FIG. 23, according to aspects of the disclosure.

FIGS. 25 and 26 illustrate cross-sectional side views of a portion of catheter system 2200 in deflated and inflated configurations, respectively. In the example of FIG. 25, eyelet 2204 is closed and the deflated interior retention/actuation balloon 2300 is positioned interior to and adjacent to (e.g., in contact with) the interior surface of the main lumen of main tubular structure 2202. In the example of FIG. 26, balloon 2300 has been inflated to expand the outer surface of main tubular structure 2202 for retention of the distal end of main tubular structure 2202 in the patient's bladder, and to open eyelets 2204. In the cross section of FIG. 26, the edges of the open eyelet 2204 have separated from contact with balloon 2300 to open a fluid pathway between main tubular structure 2202 and balloon 2300. Although this separation in the cross section of FIG. 26 may appear to show balloon 2300 floating within the main lumen of main tubular structure 2202, it should be appreciated that this is because of the particular cross section that is shown. Balloon 2300 may, for example, be formed from an expandable cavity within the inner wall of main tubular structure 2202. For example, a fluid lumen (e.g., a fluid lumen similar to fluid lumen 300 of FIG. 3) may extend along and parallel to a main lumen of main tubular structure 2202 within the wall of main tubular structure 2202, to provide fluid and/or gas for inflating balloon 2300 (e.g., by expanding the inner wall of main tubular structure 2202). Although the forgoing examples, e.g., examples of FIGS. 1-4, 8, 9, 19-23, 25 and 26 include a single retention/actuation balloon (i.e., balloon 103 and 2300) that is inflated for retention of main tubular structure 102 and 2202 in the patient's bladder and for actuating opening of eyelet(s) 104 and 2204, respectively, it should be appreciated that other configurations of a catheter system with two balloons (e.g., a retention balloon and an independent actuation balloon) are also contemplated as discussed in details below.

Figure 27:
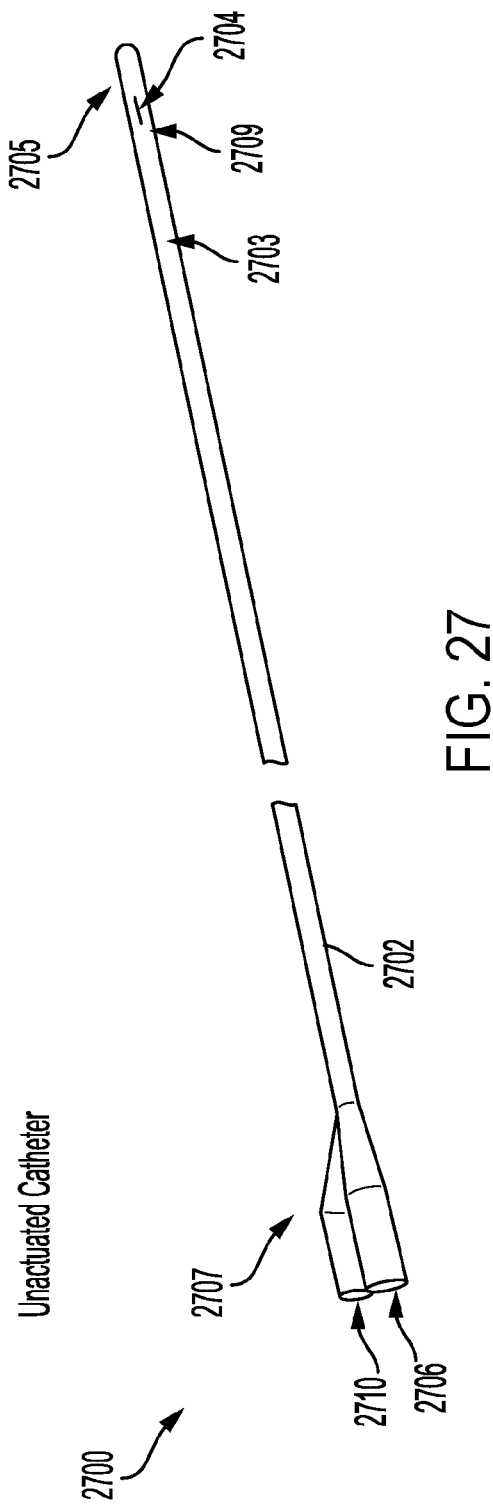
FIG. 27 represents a long-axis side view of a catheter system before introduction into a patient's bladder, according to aspects of the disclosure.
Figure 28:
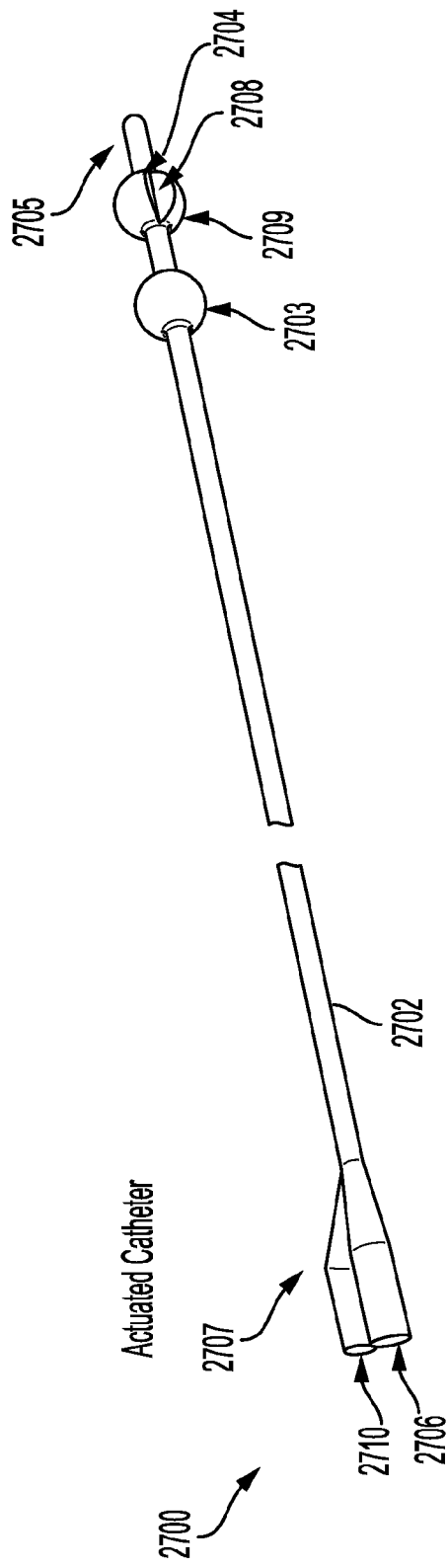
FIG. 28 represents a long-axis side view of the catheter system of FIG. 27 after introduction into the patient's bladder and inflation of a retention balloon and an actuation balloon, according to aspects of the disclosure.

FIGS. 27 and 28 illustrate long-axis views of two alternate states of a catheter system 2700, in deflated and inflated configurations, respectively, including a main tubular structure 2702, having a proximal end 2707, a distal end 2705, and an access port 2706, similar to the catheter system as shown in FIGS. 1 and 2. However, in contrast to the catheter system of the forgoing examples (e.g., examples of FIGS. 1-4, 8, 9, 19-23, 25 and 26), catheter system 2700 includes two balloons, that is a retention balloon 2703 for retention of main tubular structure 2702 in the patient's bladder, and an actuating balloon 2709, located distally relative to the retention balloon 2703, for opening an eyelet 2708 that is covered by closed fenestration 2704 as shown in FIG. 27. The retention balloon 2703 and actuating balloon 2709, deflated in the configuration of FIG. 27, are provided proximate to the distal end 2705 of main tubular structure 2702, with the actuation balloon being more distal and the retention balloon being more proximal in location along the main tubular structure.

As shown in FIG. 28, when catheter system 2700 is introduced into the patient's bladder and retention balloon 2703 and actuating balloon 2709 are inflated, e.g., by providing a fluid or a gas (e.g., water, air, saline, or another suitable biocompatible fluid or gas) into balloons 2703 and 2709, via, for example, a balloon port 2710 located at or proximate to proximal end 2707, an eyelet 2708, in line with opened fenestration 2704 (which has been pulled and/or stretched open by the inflation of actuation balloon 2709), is opened to allow fluid communication between the internal lumen of main tubular structure 2702 and the environment exterior to main tubular structure 2702. In some implementations, eyelet 2708 and fenestration 2704 are perpendicular to the long axis of main tubular structure 2702. In some implementations, eyelet 2708 and fenestration 2704 parallel to the long axis of main tubular structure 2702.

In some implementations, one balloon port (e.g., balloon port 2710) located closer to proximal end 2707 of main tubular structure 2702 is provided as shown in FIGS. 27 and 28, through which suitable inflation fluid or gas can be passed by providing a fluid or a gas (e.g., water, air, saline, or another suitable biocompatible fluid or gas) into retention balloon 2703 and actuating balloon 2709 for inflating the balloons. In some implementations, two balloon ports, e.g., a first balloon port for providing inflation fluid or gas into retention balloon 2703 for inflating balloon 2703 and a second balloon port for providing inflation fluid or gas into actuation balloon 2709 for inflating balloon 2709, are contemplated. In such implementations, inflation of retention balloon 2703 is independent of the inflation of actuating balloon 2709.

In some implementations (not shown in FIGS. 27 and 28), a first balloon port located closer to the proximal end of the main tubular structure and a secondary lumen are provided, where the secondary lumen extends along and parallel to the interior lumen between the first balloon port and the proximal end of the retention balloon, such that retention balloon 2703 is inflated by injecting an inflation fluid or gas into retention balloon 2703 through the first balloon port and the secondary lumen. In some implementations (not shown in FIGS. 27 and 28), a second balloon port located closer to the proximal end of the main tubular structure and a tertiary lumen are provided, where the tertiary lumen extends along and parallel to the interior lumen between the second balloon port and the proximal end of the actuation balloon, such that actuation balloon 2709 is inflated by injecting an inflation fluid or gas into actuation balloon 2709 through the second balloon port and the tertiary lumen. In some implementations, inflation of retention balloon 2703 is independent of the inflation of actuating balloon 2709.

In some implementations, length of main tubular structure 2702 is between 150 millimeters and 600 millimeters, for example, 450 millimeters. In some implementations, thickness of main tubular structure 2702 is between 1.0 millimeter and 15 millimeters, for example, 5 millimeters to 7 millimeters. In some implementations, retention balloon 2703 and/or actuating balloon 2709 are inflated all around the circumference of main tubular structure 2702. In some implementations, retention balloon 2703 and/or actuating balloon 2709 are inflated towards any one side of main tubular structure 2702. Further details of FIGS. 27 and 28 in cross-sectional views are provided in FIG. 29.

Figure 29:
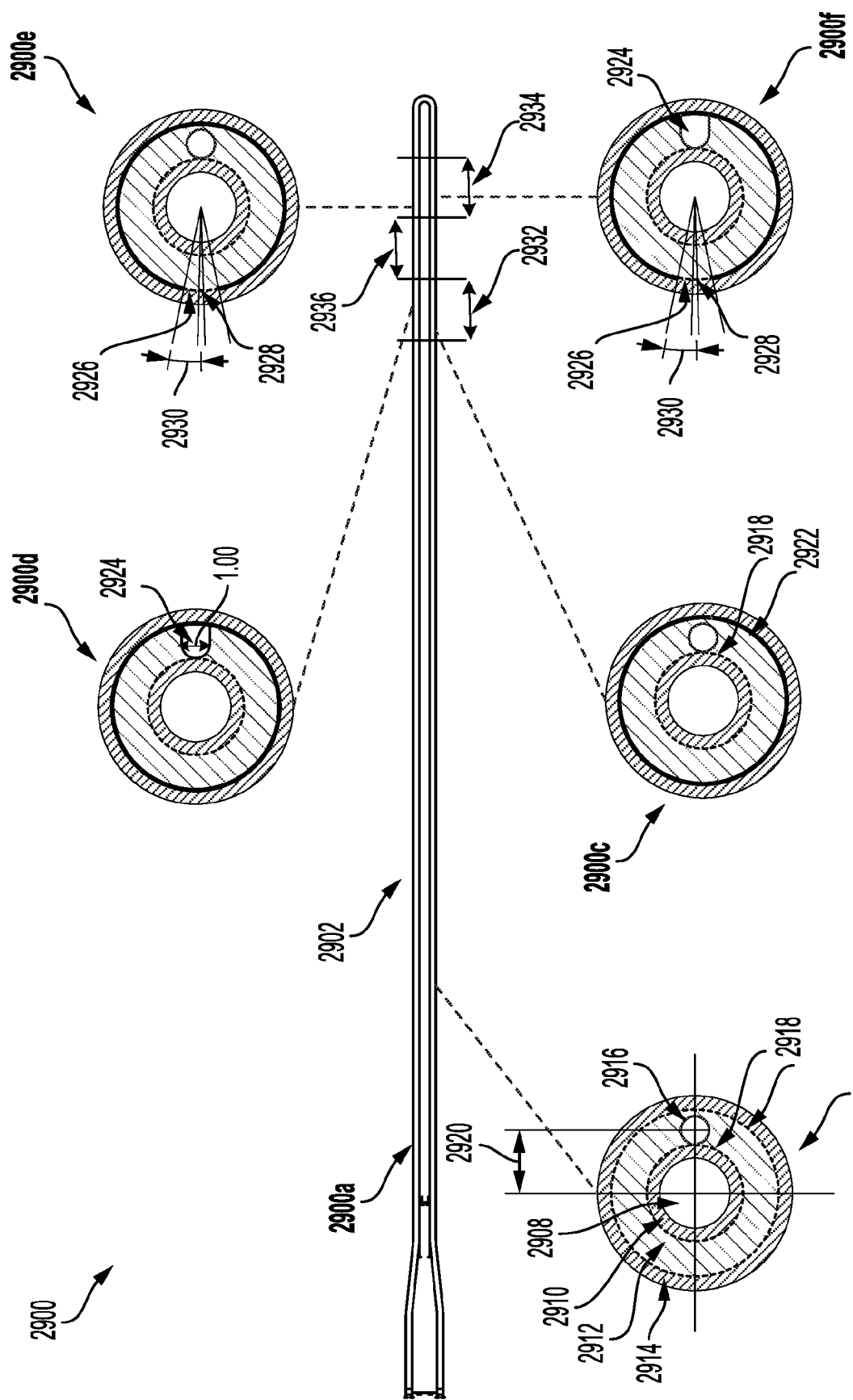
FIG. 29 represents one (1) long-axis cross-sectional view and five (5) vertical cross-sectional views of the catheter system of FIGS. 27 and 28, according to aspects of the disclosure.

FIG. 29 represents a catheter system 2900 including one (1) long-axis cross-sectional view 2900a and five (5) vertical cross-sectional views, i.e., cross-sectional view 2900b, 2900c, 2900d, 2900e and 2900f. Catheter system 2900 is similar to the catheter system of FIGS. 27 and 28. Further, main tubular structure 2902 is similar to main tubular structure 2702 of FIGS. 27 and 28 and long-axis cross-sectional view 2900a is similar to the long-axis view of the catheter system as shown in FIG. 27, except where explicitly distinguished in the description below.

Cross-sectional view 2900b illustrates an exemplary cross-section of main tubular structure 2902, and includes an internal lumen 2908, an inner layer 2910, a middle layer 2912, an outer layer 2914, an inflation lumen 2916, and two bonded interface(s) 2918, one between inner layer 2910 and middle layer 2912 and a second one between middle layer 2912 and outer layer 2914. In some implementations, internal lumen 2908 has a radius of between 1.0 millimeter and 1.4 millimeters, for example, 1.25 millimeters. In some implementations, inner layer 2910 has an outer radius of between 1.6 millimeters and 2 millimeters, for example, 1.75 millimeters, with a thickness of between 0.1 millimeter and 1.0 millimeter, for example, 0.5 millimeter. In some implementations, middle layer 2912 has an outer radius of between 2.8 millimeters and 3.2 millimeters, for example, 3 millimeters, with a thickness of between 0.5 millimeter and 3 millimeters, for example 1.25 millimeters. In some implementations, outer layer 2914 has an outer radius of between 3.4 millimeters and 3.75 millimeters, for example, 3.5 millimeters, with a thickness of between 0.1 millimeter and 1.0 millimeter, for example, 0.5 millimeter. In some implementations, inflation lumen 2916 has a radius of between 0.3 millimeter and 0.7 millimeter, for example, 0.5 millimeter, to ensure low pressure inflation of retention balloon 2703 and actuation balloon 2709. In some implementations, distance 2932 along the long-axis of main tubular structure 2702 between the distal edge and proximal edge of retention balloon 2703 is between 5 millimeters and 50 millimeters, for example, 20 millimeters. In some implementations, distance 2934 along the long-axis of main tubular structure 2702 between the distal edge and proximal edge of actuation balloon 2709 is between 5 millimeters and 50 millimeters, for example, 20 millimeters. In some implementations, distance 2936 along the long-axis of main tubular structure 2702 between the distal edge of retention balloon 2703 and the proximal edge of actuation balloon 2709 is between 1.0 millimeter and 50 millimeters, for example, 20 millimeters.

It is understood that the cross-section of main tubular structure 2902 remains the same as cross-sectional view 2900b until reaching combined retention/actuation balloon 103 or retention balloon 2703, or unless explicitly distinguished. In some implementations, the cross-section of main tubular structure 2902 reverts back to the cross-sectional view 2900b, for example, in the distal end of main tubular structure 2902 after the actuation balloon 2709.

Main tubular structure 2702 and 2902, including any of the layers of the catheter system, e.g., inner layer 2910, middle layer 2912, and outer layer 2914, may be formed from any flexible or semi-flexible material including latex, silicone, or Teflon or any polymer that is biocompatible with a subject's body and will not cause undue discomfort. Outer layer 2914 may be formed from the same material as main tubular structure 2702 and 2902 or a different material (e.g., a different one, or a different combination, of latex, silicone, or Teflon or any polymer that is biocompatible with a subject's body and will not cause undue discomfort).

In some implementations, retention balloon 2703 and actuation balloon 2709 are inflated by introducing an inflation fluid (e.g., water, air, saline, or another suitable biocompatible fluid or gas) through the secondary and tertiary lumens, as applicable, at a pressure of between 0.1 psi and 5 psi, for example, 0.5 psi. In some implementations, thickness 2920 between the center of internal lumen 2908 and the center of inflation lumen 2916 is between 1.5 millimeters and 2.5 millimeters, for example, 2.25 millimeters. It should be understood that internal lumen 2908, inner layer 2910, middle layer 2912, outer layer 2914, inflation lumen 2916, and the two bonded interface(s) 2918 between inner layer 2910 and between middle layer 2912 and between middle layer 2912 and outer layer 2914, may be provided in a range of suitable radius and thicknesses to effectively control the low pressure required for inflating the balloons, as long as the provided radius and/or thickness does not cause any undue discomfort inside a patient's cavity.

Cross-sectional view 2900c illustrates an exemplary cross-section of main tubular structure 2902 located towards the proximal end of retention balloon 2703, and is the same as and includes the same components as cross-sectional view 2900b, except that the interface between inner layer 2910 and middle layer 2912 is a bonded interface 2918 and the interface between middle layer 2912 and outer layer 2914 is an unbonded interface 2922. Unbonded interface 2922, when present, allows retention balloon 2703 and/or actuation balloon 2709 to inflate.

Cross-sectional view 2900d illustrates an exemplary cross-section of main tubular structure 2902 located towards the distal end of retention balloon 2703, and is the same as and includes the same components as cross-sectional view 2900c, except that inflation lumen 2924 extends through the thickness of middle layer 2912 to the outer layer 2914 of main tubular structure 2902 for inflating retention balloon 2703. In some implementations, the thickness of inflation lumen 2924 is between 0.8 millimeter and 1.2 millimeters, for example, 1 millimeter, in diameter.

Cross-sectional view 2900e illustrates an exemplary cross-section of main tubular structure 2902 located towards the proximal end of actuation balloon 2709, and is the same as and includes the same components as cross-sectional view 2900c, except that the interface between middle layer 2912 and outer layer 2914, that is unbonded interface 2922, does not go all the way around the circumference of the middle and outer layers. Instead, a short bonded region 2926 is included between middle layer 2912 and outer layer 2914 of the main tubular structure 2902 on either side of a centerline of an eyelet 2928 in cross-sectional view 2900e. When actuation balloon 2709 is in the deflated configuration, eyelet 2928 is covered by a portion of the outer layer 2914 that includes a fenestration 2704 through its thickness (as shown in FIG. 27). When actuation balloon 2709 is inflated, fenestration 2704 (as shown in FIG. 28) is pulled and/or stretched into an open configuration, a space between middle layer 2912 and outer layer 2914 of the main tubular structure 2902 where the interface is unbonded fills with the inflation fluid, inflating the actuation balloon 2709. In the open configuration as shown in FIG. 28, eyelet 2928 in main tubular structure 2902 is exposed to the exterior environment (e.g., the interior of the patient's bladder) by the opened fenestration. In this way, fluid such as urine within the patient's bladder can be allowed to pass through fenestration and eyelet 2928 into interior lumen 2908 of main tubular structure 2902. In some implementations, insertion of the distal end of main tubular structure 2902 into other fluid reservoirs, e.g., fluid reservoirs outside of a human or animal body, such as fluid reservoirs in chemical reactors, HVAC systems, or other pieces of industrial or scientific equipment, may allow collecting or sampling of fluids from the other fluid reservoirs through the eyelet and the interior lumen. In some implementations, eyelet 2928, when open, results in an opening or slit 2930 between 5 degrees and 15 degrees, for example 10 degrees, on either side of a center line of the eyelet 2928 around the circumference of catheter system 2900.

Cross-sectional view 2900*f* illustrates an exemplary cross-section of main tubular structure 2902 located towards the distal end of actuation balloon 2709, and is the same as and includes the same components as cross-sectional view 2900*e*, except that inner lumen 2924 extends through the thickness of middle layer 2912 to outer layer 2914 of main tubular structure 2902, as described for cross-sectional view 2900*d*. As described for cross-sectional view 2900*e*, when actuation balloon 2709 is in the deflated configuration, eyelet 2928 is covered by a portion of the outer layer 2914 that includes a fenestration 2704 through its thickness (as shown in FIG. 27). When actuation balloon 2709 is inflated, fenestration 2704 (as shown in FIG. 28) is pulled and/or stretched into an open configuration, a space between middle layer 2912 and outer layer 2914 of the main tubular structure 2902 where the interface is unbonded fills with the inflation fluid, inflating the actuation balloon 2709. In the open configuration as shown in FIG. 28, eyelet 2928 in main tubular structure 2902 is exposed to the exterior environment (e.g., the interior of the patient's bladder) by the opened fenestration. In this way, fluid such as urine within the patient's bladder can be allowed to pass through fenestration and eyelet 2928 into interior lumen 2908 of main tubular structure 2902. In some implementations, insertion of the distal end of main tubular structure 2902 into other fluid reservoirs, e.g., fluid reservoirs outside of a human or animal body, such as fluid reservoirs in chemical reactors, HVAC systems, or other pieces of industrial or scientific equipment, may allow collecting or sampling of fluids from the other fluid reservoirs through the eyelet and the interior lumen. In some implementations, eyelet 2928, when open, results in an opening or slit 2930 between 5 degrees and 15 degrees, for example 10 degrees, on either side of a center line of the eyelet 2928 around the circumference of catheter system 2900.

The subject matter disclosed herein also relates to a method of use of a catheter system. The method includes advancing proximally-to-distally a main tubular structure (see, e.g., main tubular structures 102, 2202, 2702 or 2902) of a catheter system into a subject in need of catheterization. The catheter system may be advanced into an existing orifice of a subject, or an orifice that is created before beginning the procedure. The pre-existing orifice may be a urethra, an anus, a vagina, or other orifice that normally exists; the pre-existing orifice may also be an injury or wound, such as a stoma or fistula. The subject may be any animal, including humans as well as non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, poultry, and horses, or pets, such as dogs and cats. Furthermore, the subject may be of any species, gender, age, ethnic population, or genotype. Accordingly, the term subject includes males and females, and it includes elderly, elderly-to-adult transition age subjects, adults, adult-to-pre-adult transition age subjects, and pre-adults, including adolescents, children, toddlers, and infants. The term subject also includes a subject of any body height, body weight, or any organ or body part size or shape.

Following insertion into an orifice, the catheter system is advanced proximally-to-distally, until a distal end, including a combined retention/actuation balloon or a distal end with two balloons (e.g., a retention balloon for retention of the main tubular structure of the catheter in the patient's bladder and a separate actuation balloon, located distally to the retention balloon, for opening an eyelet) and at least one closed eyelet, is disposed in a cavity of the subject. The retention and/or actuation balloon(s) can then be inflated (e.g., by injecting an inflating fluid or gas into the retention and/or actuation balloon via a secondary lumen or a tertiary lumen that runs from a balloon port, along a main lumen in the main tubular structure, to either the combined retention/actuation balloon or the two respective retention and actuating balloon(s)), to help retain the main tubular structure in the cavity. Inflating the balloon(s) (the combined retention/actuation balloon or the actuation balloon) also causes the at least one eyelet to be opened to allow fluid flow between the subject cavity and the main lumen of the main tubular structure.

The combined retention/actuation balloon or the actuation balloon may open the eyelet by pulling open a fenestration in an outer layer that is disposed on the outer surface of the main tubular structure, by directly pulling open the eyelet itself, and/or by pushing open the eyelet from within the main lumen. Fluid may then be allowed to flow into the main lumen to an access point at a proximal end of the main tubular structure.

The access point may include a dilating diaphragm, or other structure or valve, which prevents the fluid from draining through the access point. An access cap having a beak with beak eyelets may be attached to the proximal end of the main tubular structure (e.g., at an access port comprising the access point diaphragm), so that the beak opens the access point to allow the fluid to flow into a cavity in the access cap via the beak eyelets, and out of the catheter system via an opening at the proximal end of the access cap. The access cap can be intermittently removed and/or replaced to allow the patient cavity to intermittently fill and empty, and/or to couple the access port to a different type of container or other drainage destination.

Using this method, a catheter system can allow catheterization of a subject with reduced risk of catheter-associated UTI. In some embodiments, the operator withdraws the catheter system from the subject. The operator can be a doctor, nurse, other medical practitioner, medical providers in a clinical or homecare setting, or anyone trained to deploy the catheter system. The catheter system may also be deployed by a multiple operators, for example, medical practitioners working in a team.

In the above description, reference is made to the accompanying drawings that form a part hereof, and in which is shown by way of illustration specific embodiments, which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

The following statements are potential claims that may be converted to claims in a future application. No modifications of the following statements should be allowed to affect the interpretation of claims, which may be drafted when this provisional application is converted into a regular utility application.

What is claimed is:

1. A catheter system comprising:
 a main tubular structure having an interior lumen, a proximal end, and a distal end;
 an actuation balloon located closer to the distal end than to the proximal end; and
 an eyelet, located proximate to the actuation balloon, that extends through the main tubular structure from an exterior surface through to the interior lumen, wherein the eyelet is configured to be closed when the actuation balloon is in a deflated configuration and to be opened by inflation of the actuation balloon to an inflated configuration; and
 an outer layer disposed on the exterior surface of the main tubular structure, wherein the outer layer comprises a fenestration aligned with the eyelet, wherein the outer layer is configured to be pulled by the inflation of the actuation balloon, and wherein the fenestration is configured to be pulled open by the pull on the outer layer to open the eyelet.

2. The catheter system of claim 1, wherein the actuation balloon is also a retention balloon.

3. The catheter system of claim 1, wherein the system further comprises a retention balloon distinct from the actuation balloon.

4. The catheter system of claim 3, wherein the retention balloon is located proximally with respect to the actuation balloon along the main tubular structure.

5. The catheter system of claim 2, further comprising a balloon port located proximate to the proximal end of the main tubular structure, and a secondary lumen, wherein the secondary lumen extends along and parallel to the interior lumen between the balloon port and the proximal end of the actuation balloon.

6. The catheter system of claim 4, further comprising a balloon port located proximate to the proximal end of the main tubular structure, and a secondary lumen, wherein the secondary lumen extends along and parallel to the interior lumen between the balloon port and a proximal edge of the retention balloon and between a distal edge of the retention balloon and a proximal edge of the actuation balloon, and wherein the actuation balloon and the retention balloon are inflated by injecting an inflation fluid or gas into both the actuation balloon and the retention balloon through the balloon port and the secondary lumen.

7. The catheter system of claim 4, further comprising:
 a first balloon port located proximate to the proximal end of the main tubular structure, and a secondary lumen, wherein the secondary lumen extends along and parallel to the interior lumen between the first balloon port and the retention balloon, wherein the retention balloon is inflated by injecting an inflation fluid or gas into the retention balloon through the first balloon port and the secondary lumen; and
 a second balloon port located proximate to the proximal end of the main tubular structure, and a tertiary lumen, wherein the tertiary lumen extends along and parallel to the interior lumen between the second balloon port and the actuation balloon, wherein the actuation balloon is inflated by injecting an inflation fluid or gas into the actuation balloon through the second balloon port and the tertiary lumen.

8. The catheter system of claim 7, wherein the catheter system is configured such that inflation of the retention balloon is independent of inflation of the actuating balloon.

9. The catheter system of claim 1, further comprising an access port located proximate to the proximal end of the main tubular structure.

10. The catheter system of claim 9, wherein the access port comprises a dilating diaphragm having a resting configuration in which an access point in the dilating diaphragm is closed to prevent fluid from flowing from the interior lumen through the access port.

11. The catheter system of claim 10, further comprising an access cap configured to couple to the access port, and to open the access point in the dilating diaphragm when coupled to the access port.

12. The catheter system of claim 11, wherein the access cap comprises a base, a beak extending from the base, and at least one beak eyelet extending through the beak to a cavity formed within the beak.

13. The catheter system of claim 12, wherein the beak is configured to press open the access point of the dilating diaphragm, and to extend through the dilating diaphragm so that, when the access cap is coupled to the access port, the at least one beak eyelet fluidly couples the interior lumen of the main tubular structure to the cavity within the beak.

14. The catheter system of claim 13, wherein the cavity within the beak extends through the base of the access cap to an opening located proximate to the proximal end of the access cap, wherein the opening is configured to be coupled to one of a plurality of drainage destinations.

15. A method, comprising:
 inserting, into a bladder of a patient, a distal end of a main tubular structure having an interior lumen, a proximal end, a distal end, and an outer layer disposed on an exterior surface of the main tubular structure, wherein the outer layer comprises a fenestration aligned with an eyelet passing through the main tubular structure from the exterior surface of the main tubular structure to the interior lumen of the main tubular structure;
 inflating an actuation balloon located proximate to the distal end of the main tubular structure and proximate the fenestration in the outer layer; and
 opening the eyelet by inflating the actuation balloon, wherein inflating the actuation balloon pulls on the outer layer to open the fenestration, thereby opening the eyelet.

16. The method of claim 15, wherein the actuation balloon is also a retention balloon.

17. The method of claim 15, further comprising inflating a retention balloon that is distinct from the actuation balloon, wherein the retention balloon is located proximally with respect to the actuation balloon along the main tubular structure.

18. The method of claim 17, wherein the retention balloon and the actuation balloon are inflated by injecting an inflation fluid or gas into the balloons through a single balloon port.

19. The method of claim 17, wherein the retention balloon and the actuation balloon are inflated by injecting an inflation fluid or gas into the balloons through two separate balloon ports, wherein inflation of the retention balloon is independent of the inflation of the actuating balloon.

20. The method of claim 15, further comprising, preventing fluid from flowing from the interior lumen through an access port proximate to the proximal end of the main tubular structure, with a dilating diaphragm proximate to the proximal end of the main tubular structure.

21. The method of claim 20, further comprising coupling an access cap to the access port to allow the fluid to flow from the interior lumen through the access port and the access cap.

22. The method of claim 21, wherein coupling the access cap to the access port comprises passing a beak of the access cap through the dilating diaphragm until a beak eyelet on the beak fluidly couples the interior lumen to a cavity within the access cap.

23. The method of claim 21, wherein coupling the access cap to the access port comprises engaging a pair of flanges on the access cap with corresponding mounting features on the access port.

24. The method of claim 23, further comprising removing the access cap, to prevent flow of the fluid from the interior lumen through the access port.

25. The method of claim 24, wherein removing the access cap comprises pinching a pair of tabs to disengage the pair of flanges from the corresponding mounting features.

\* \* \* \* \*